United States Patent
Javadi et al.

(10) Patent No.: US 9,952,136 B2
(45) Date of Patent: *Apr. 24, 2018

(54) SYSTEMS AND METHODS FOR DETECTING A PARTICLE

(71) Applicant: STRATEDIGM, INC., San Jose, CA (US)

(72) Inventors: Shervin Javadi, Monte Sereno, CA (US); Arjuna Karunaratne, Fremont, CA (US)

(73) Assignee: STRATEDIGM, INC., San Jose, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 14/990,740

(22) Filed: Jan. 7, 2016

(65) Prior Publication Data

US 2016/0209318 A1    Jul. 21, 2016

Related U.S. Application Data

(60) Provisional application No. 62/106,164, filed on Jan. 21, 2015.

(51) Int. Cl.
*G01N 15/14* (2006.01)

(52) U.S. Cl.
CPC ..... *G01N 15/1425* (2013.01); *G01N 15/1434* (2013.01); *G01N 15/1459* (2013.01); *G01N 2015/1438* (2013.01)

(58) Field of Classification Search
CPC ........... G01N 15/1425; G01N 15/1459; G01N 2015/1438
See application file for complete search history.

(56) References Cited

U.S. PATENT DOCUMENTS

| | | | | |
|---|---|---|---|---|
| 4,573,796 A | * | 3/1986 | Martin | G01N 15/1429 250/461.2 |
| 5,158,889 A | | 10/1992 | Hirako et al. | |
| 5,682,038 A | * | 10/1997 | Hoffman | G01N 15/14 250/226 |
| 7,440,101 B2 | * | 10/2008 | Auer | G01N 15/14 250/458.1 |
| 7,692,773 B2 | * | 4/2010 | Roth | G01N 15/1434 356/28 |
| 7,990,525 B2 | | 8/2011 | Kanda | |

(Continued)

OTHER PUBLICATIONS

International Search Report, dated May 13, 2016, for corresponding International Patent Application No. PCT/US2016/012523, 5 pages.

(Continued)

*Primary Examiner* — Dominic J Bologna
(74) *Attorney, Agent, or Firm* — Kilpatrick Townsend & Stockton LLP

(57) ABSTRACT

A cytometry system having a computing system. The system includes a plurality of lasers controlled by the computing system to emit laser light. Each laser is spatially separated along a flow stream path. A detector system configured to receive light pulses from the plurality of lasers. The detector system being coupled to sampling circuitry. The computing system is configured to operate each of the plurality of lasers to independently emit laser light with respect to one another according to time of flight intervals along the flow stream path.

13 Claims, 5 Drawing Sheets

(56) References Cited

U.S. PATENT DOCUMENTS

| | | | | |
|---|---|---|---|---|
| 8,570,500 | B2* | 10/2013 | Javadi | G01N 15/1434 |
| | | | | 356/246 |
| 2003/0204330 | A1* | 10/2003 | Allgeyer | A61B 5/0059 |
| | | | | 702/32 |
| 2004/0057050 | A1* | 3/2004 | Beck | G01N 15/1459 |
| | | | | 356/336 |
| 2010/0220315 | A1* | 9/2010 | Morrell | G01N 15/1436 |
| | | | | 356/73 |
| 2012/0044480 | A1* | 2/2012 | Javadi | G01N 15/1434 |
| | | | | 356/73 |

OTHER PUBLICATIONS

Written Opinion, dated May 13, 2016, for corresponding International Patent Application No. PCT/US2016/012523, 5 pages.

* cited by examiner

SYSTEMS AND METHODS FOR DETECTING A PARTICLE

CROSS-REFERENCES TO RELATED APPLICATIONS

This application claims the benefit of U.S. Provisional Application No. 62/106,164, filed on Jan. 21, 2015, which is incorporated by reference herein.

BACKGROUND OF THE INVENTION

The invention is related to flow cytometry systems, and more specifically, detector arrangements for flow cytometry systems.

Flow cytometry systems are used to analyze aspects of microscopic particles, such as cells or cell sized particles. A typical flow cytometry system includes a laser aligned with a flow stream of the microscopic particles. The laser is arranged to emit a beam of light of a single wavelength at the particle which is moving in a hydrodynamically-focused stream of fluid. Typically, a number of detectors collect forward scattered, side scattered, and fluoresced light caused by the intersection of the laser beam and particle. Information derived from the collected light can be used to produce histograms, which provide physical and chemical characteristics of the particles.

Complex cytometry systems typically make use of multiple detectors which provide electrical signals derived from the collected light. The detectors are mounted to emissions modules, with each module being mechanically affixed to a particular laser via fiber optics or a pin hole arrangement. The module can provide a certain filtered wavelength of light to each detector via optics. Thus, each detector is mechanically affixed to a particular laser, and each laser requires an emissions module. When it is desired to process multiple events caused by multiple lasers, then a complex system is required, as scaling up measurement capabilities requires the addition of many detectors. Accordingly, current multiple laser cytometry systems often possess little flexibility, large size, and high cost. Prior systems have proposed using a single detector for multiple laser sources with some success. However, such systems require complex signal processing to avoid signal cross talk between lasers and errant particles. Accordingly, there is a need for improving current multiple cytometry systems.

BRIEF SUMMARY OF THE INVENTION

Some embodiments of the invention are directed to a cytometry system having a computing system. A plurality of lasers is controlled by the computing system to emit laser light. Each laser is spatially separated along a flow stream path. A detector system is configured to receive light pulses from the plurality of lasers, the detector system being coupled to the computing system. The computing system can be configured to operate each of the plurality of lasers to independently emit laser light with respect to one another according to time of flight intervals along the flow stream path.

In some embodiments, the plurality of lasers includes at least a first laser and a last laser.

In some embodiments, the plurality of lasers comprises at least a second laser spatially separated between the first and last laser.

In some embodiments, the computing system is configured to turn the first laser ON only when the last laser is OFF.

In some embodiments, after turning the first laser ON, the computing system is configured to turn the first laser OFF and the last laser ON according to the time of flight internals.

In some embodiments, the computing system is configured to turn the first laser ON again only after the last laser is turned OFF according to the time of flight internals.

Some embodiments of the invention are directed to a method for operating a cytometry system. In the method, a material is flowed along a flow stream having a first interrogation point of a first laser spatially separated from a last interrogation point of a second laser. The first laser is turned ON and the second laser is turned OFF. A first light pulse is received that is derived from the first laser interacting with a material at the first interrogation point. Based on receiving the first light pulse, the second laser is turned ON. Afterwards, a second light pulse is received that is derived from the second laser interacting with the material. Based on receiving the second light pulse and or time of flight, the second laser is turned OFF.

In some embodiments, based on receiving the second light pulse and or time of flight, the first laser is turned back ON.

In some embodiments, the flow stream includes a third interrogation point of at least a third laser downstream from the second interrogation point.

In some embodiments, based on receiving the second light pulse and or time of flight, the third laser is turned ON.

In some embodiments, a third light pulse is received that is derived from the third laser interacting with the material.

In some embodiments, based on receiving the third light pulse and or time of flight, the third laser is turned OFF.

In some embodiments, based on receiving the third light pulse, the first laser is turned back ON.

These and other embodiments of the invention are described in further detail below, which provides an exemplary implementation of the embodiments and aspects disclosed herein.

DETAILED DESCRIPTION OF THE INVENTION

Figure 1A:
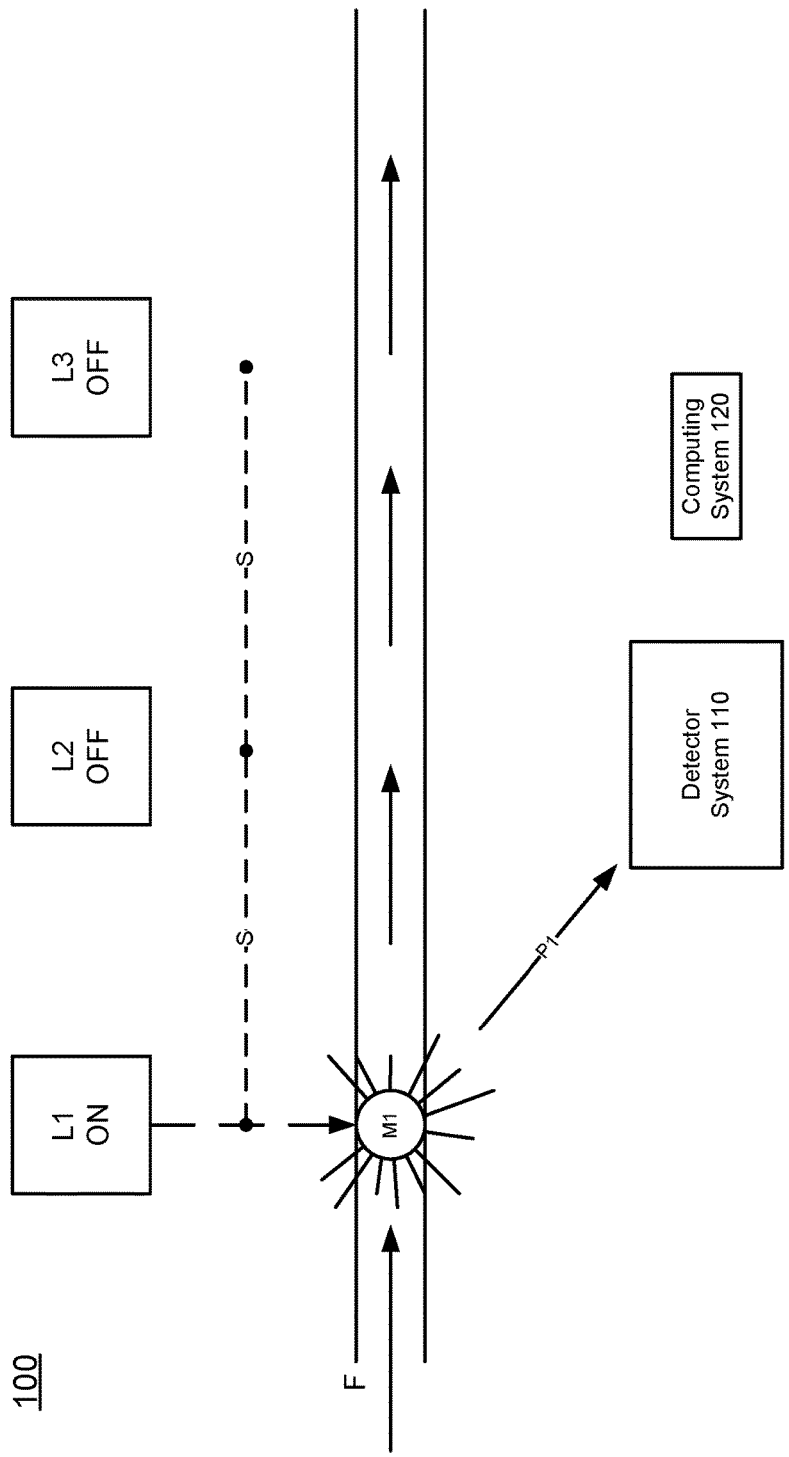
FIGS. 1A-1C are simplified schematic views of a cytometry system, according to an embodiment of the invention.

FIG. 1A shows a simplified cytometry system 100, according to an embodiment of the invention. It should be understood that certain aspects (e.g. optics, emissions modules) common to flow cytometry systems are not included for the sake of brevity. The system 100 includes a plurality of lasers L1, L2, L3. The lasers L1, L2, L3 can be configured to emit different wavelengths of laser light at different power levels. Some exemplary wavelengths include 488 nm (40 mW), 640 nm (50 mW), 405 nm (50 mW), 372 nm (20 mW), 561 nm (50 mW), and 532 nm (50 mW). It should be understood that while only three lasers are shown, more or less may be utilized by the system 100.

The lasers L1, L2, L3 are spatially separated, as indicated by distance S, along a flow stream path F. The flow stream path F is a fluid passage for transportation of material M, which may be an individual biological cell-sized particle or a biological cell. The flow stream F may be sized to only allow one individual portion of material M to occupy the cross-section of the flow stream path F. In some embodiments, the system may hydrodynamically focus (i.e., funnels) under pressure a plurality of the material M into the flow stream F so that only one individual portion of material M is passed into the flow stream F at a time. In other embodiments, hydrodynamic focusing is not implemented, and a simple flow stream is used.

The lasers L1, L2, L3 are configured to emit laser light at the flow stream F at respective interrogation points. At these interrogation points laser light intersects the material M1, for example at a 90° angle. A detector system 110 (e.g. including a light condenser lens and signal processing circuitry) collects side scattered, and/or fluoresced pulses of light P1, P2, P3 that are derived from the intersection of laser light and the material M. Accordingly, each pulse of light P1, P2, P3 may include a plurality of different directional intensities and/or wavelengths.

The detector system 110 is configured to receive the pulses of light P1, P2, P3 derived from the plurality of lasers L1, L2, L3 at distinct time intervals, according to when the pulses of light P1, P2, P3 are generated and received. The detector system 110 may include a photodiode or a photo multiplier tube and includes associated amplifying and triggering circuitry. The arrival of pulse P1 to the detector system 110 creates one or more pulse signals (e.g., voltage, current) that may be proportionally derived from pulse P1. The pulse signal can be amplified and adjusted by the detector system 110, which further causes the occurrence of one or more triggering events. The computing system 120 is electronically coupled to all aspects of the system 100 for operational control thereof. It should be understood, that while three lasers are shown, only two are required, i.e., a first laser and a last laser, with no or any number of lasers there between. Additional detector systems are disclosed in related U.S. Pat. No. 8,570,500, which is incorporated by reference.

The computing system 120 is configured to control each of the lasers L1,3,L3 independently with respect to one another. Put another way, only one of the lasers L1,L2,L3 is configured to emit laser light at one given instance to prevent errant material from causing signal interference, which is iteratively shown by FIGS. 1A-1C. At FIG. 1A, particle M1 passes through the interrogation point of laser L1. This causes an emission of a pulse of light P1 as the laser light reacts with the particle. The detector system 110 receives the pulse of light P1 and processes the signal accordingly. This event also acts as a trigger to shut off laser L1 and turn on laser L2 as shown at FIG. 1B.

The computing system turns laser L2 on according to the time of flight of the particle M1, which is known according to the time of flight interval between the interrogation points of the lasers L1 and L2. The time of flight is known and effectively constant, and is calculated from the flow rate of the material M1 and the fixed distance S of the spatial separation between the interrogations points of L1 and L2. When M arrives at the interrogation point of L2, the process may then repeat (i.e., turn on L3, turn off L2, L1 remains off), and so on at the interrogation point of L3 as shown at FIG. 1C.

Figure 1B:
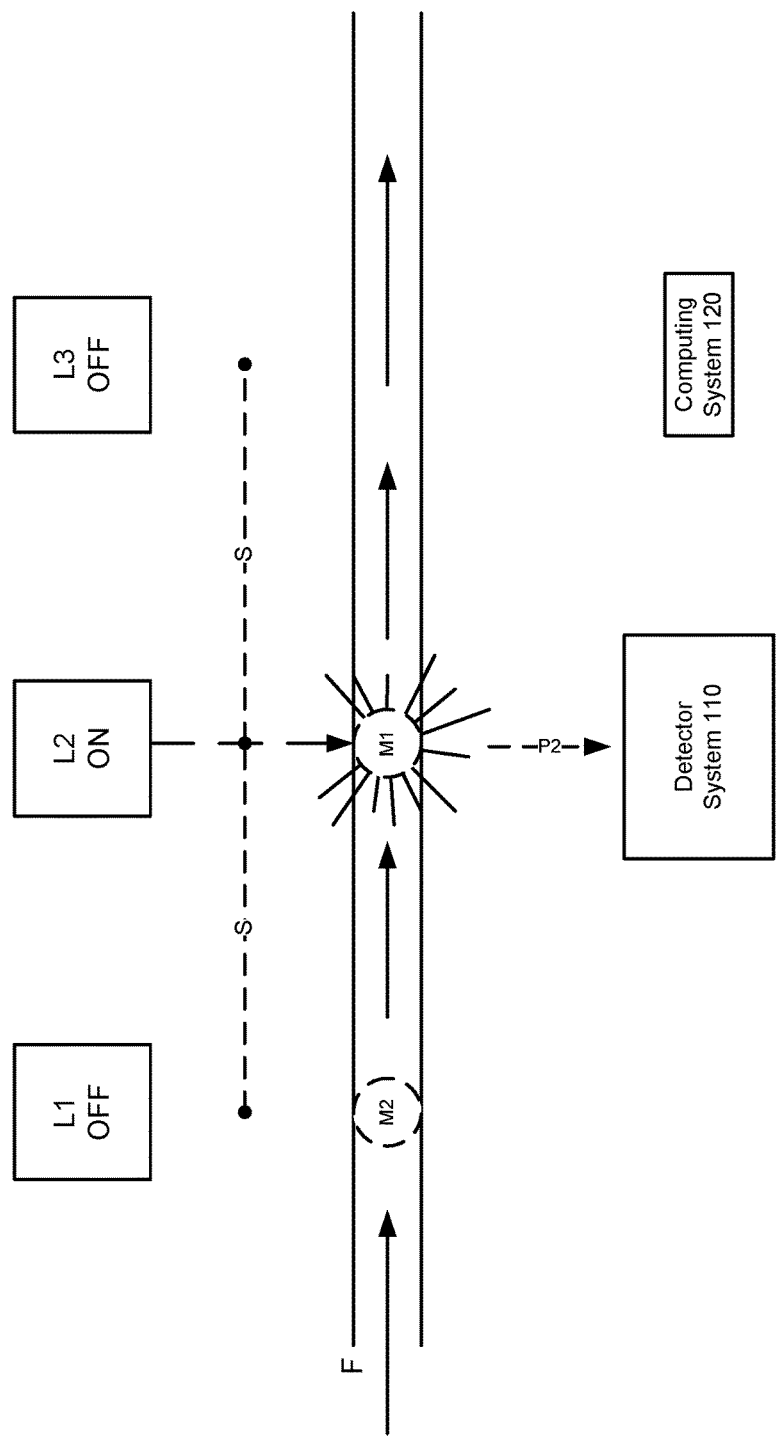
Figure 1C:
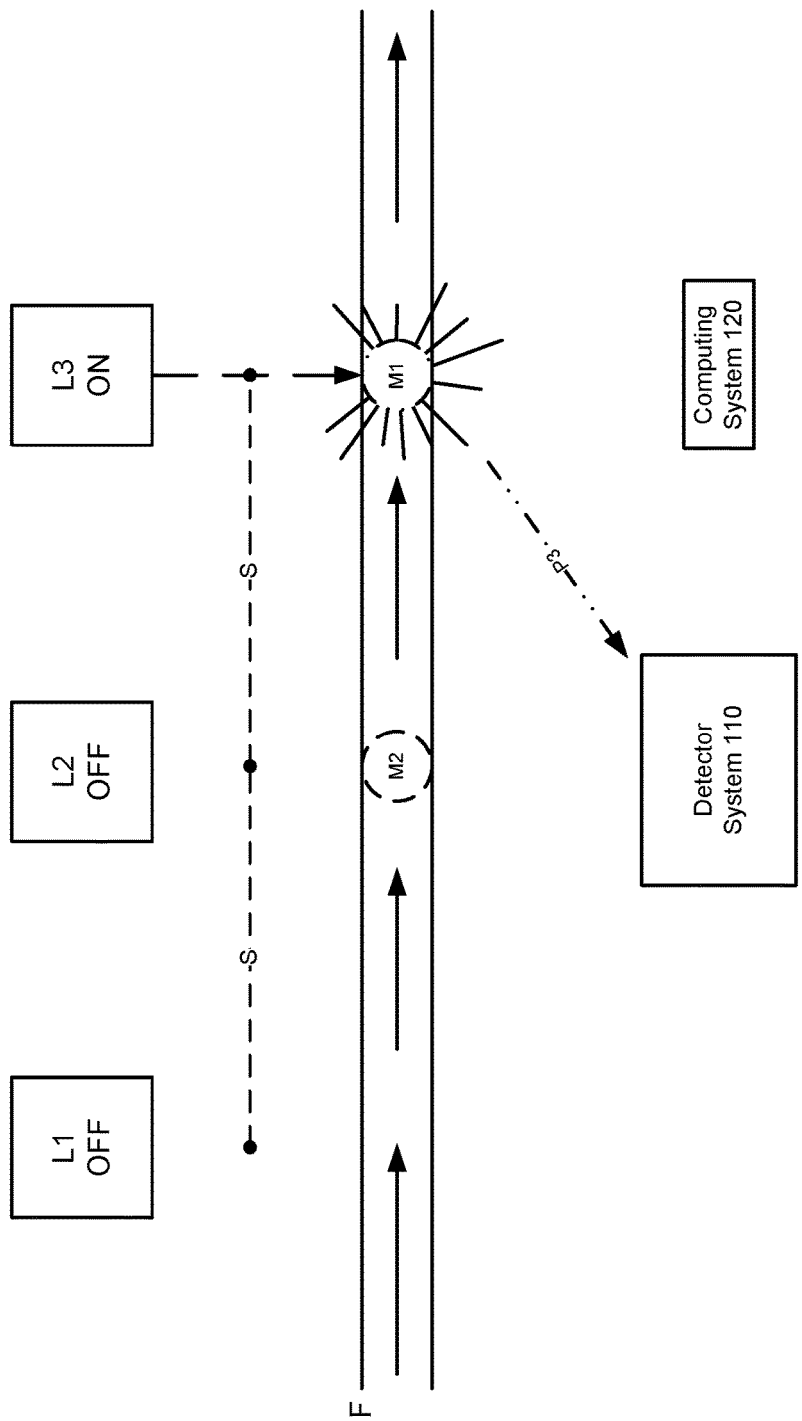

The system 100 is advantageous because errant particles, such as material M2 shown at FIGS. 1B and 1C will not cause an event by interacting with a laser when M1 is interacting with another laser. Accordingly, per system 100, errant material will not cause signal interference with other lasers.

Figure 2:
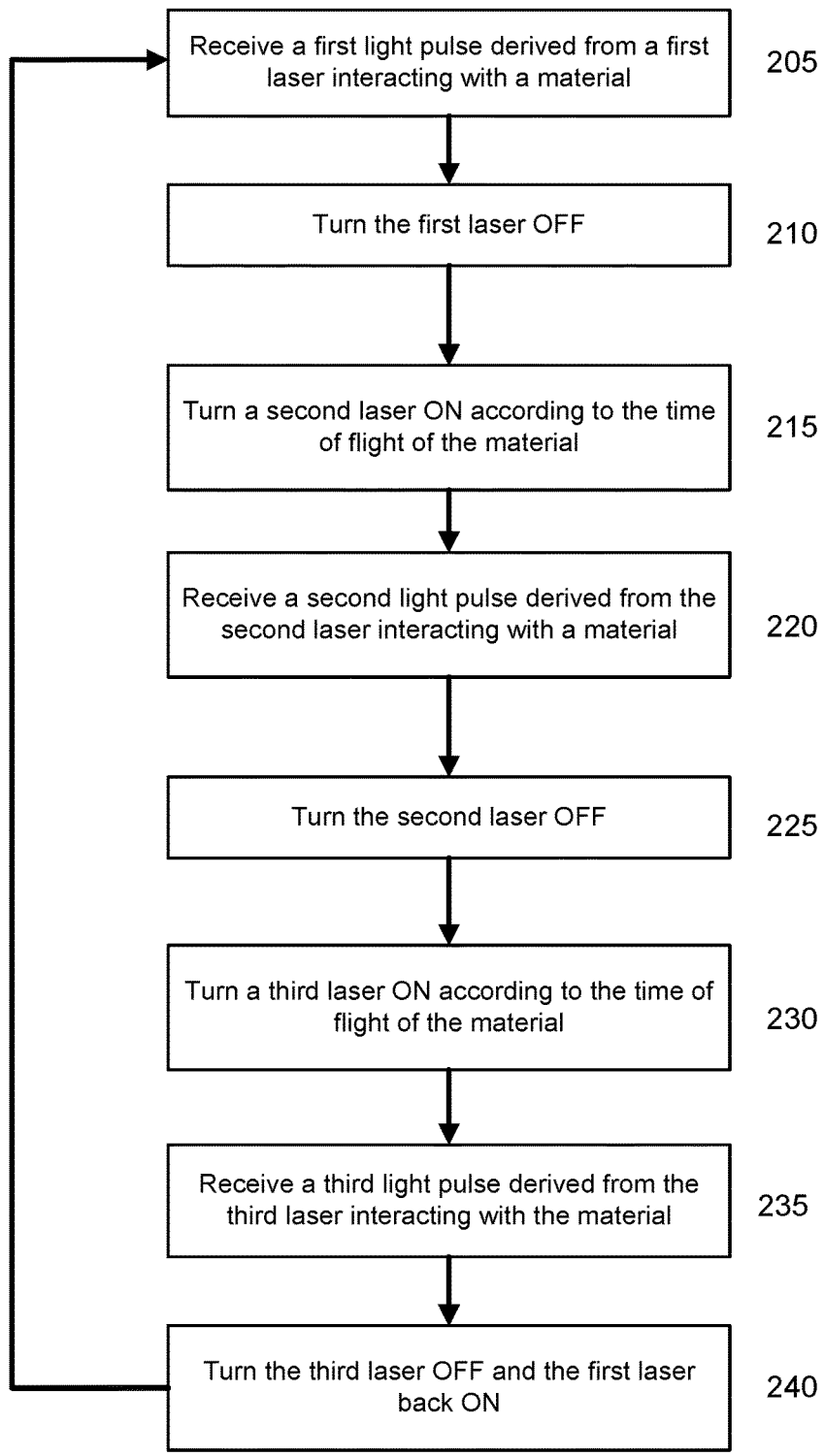
FIG. 2 is a flow chart for a method of operating a cytometry system, according to an embodiment of the invention.

FIG. 2 shows a method 200 for operating a cytometry system, according to an embodiment of the invention. It should be understood that method 200 can be implemented, in part or whole, in conjunction with any of the systems and/or subsystems disclosed herein.

At operation 205 a first light pulse signal is received by a cytometry measurement system, having at least a first laser and a last laser, and in this specific example, first laser, a second laser, and a third laser, each with respective interrogation points spatially separated along a flow stream of material. The first light pulse signal is derived from the intersection of laser light from the first laser with a material at an interrogation point, by collecting scattered (side and front) and/or fluoresced light which is routed via optics to a detector, e.g., a photodiode or photomultiplier. Thus, the photodiode or photomultiplier generates a proportional signal (e.g., voltage, current) of the collected light. The first light pulse signal can be processed by amplification circuitry and to signal processing circuitry (i.e., a sampling circuit), or alternatively stored for later processing. It should be understood that "light pulse signal" is intended to include informational signals derived from the collected reflected and/or fluoresced light, which may be further processed by amplification, normalization, and/or digitizing circuits.

At operation 210, the first light pulse signal is received by a detection system. This event is a trigger to turn the first laser OFF before the material intersects the interrogation point of the second laser. In addition, or alternatively, the first laser can be turned OFF based on the time of flight of the material, before the material intersects the interrogation point of the second laser.

At operation 215, receiving the first light pulse signal triggers also triggers turning the second laser ON before the material intersects the interrogation point of the second laser. The interrogation points of the lasers are spatially separated, thus the second laser is turned ON on according to the time of flight of the material, which is known according to the interval between the interrogation points of the lasers. The time of flight is known and effectively constant, and is calculated from the flow rate of the material and the fixed distance of the spatial separation between the interrogations points of the lasers.

At operation 220, a second light pulse signal is derived from the second laser interacting with the material. Pulse information may then derived from the second light pulse or alternatively the value of the second light pulse signal can be stored for later processing. This event and or time of flight is also a trigger to turn the second laser OFF before the material intersects the interrogation point of the third laser, as shown in operation 225.

At operation 230, receiving the second light pulse signal and/or time of flight is also an event that triggers turning the third laser ON before the material intersects the interrogation point of the third laser. At operation 235, a third light pulse signal is derived from the third laser interacting with the material. Pulse information can then derived from the third light pulse or alternatively the value of the third light pulse signal can be stored for later processing. This event and/or time of flight is also a trigger to turn the third laser OFF and the first laser back ON at operation 240. Accordingly, the process can repeat with new material.

Figure 3:
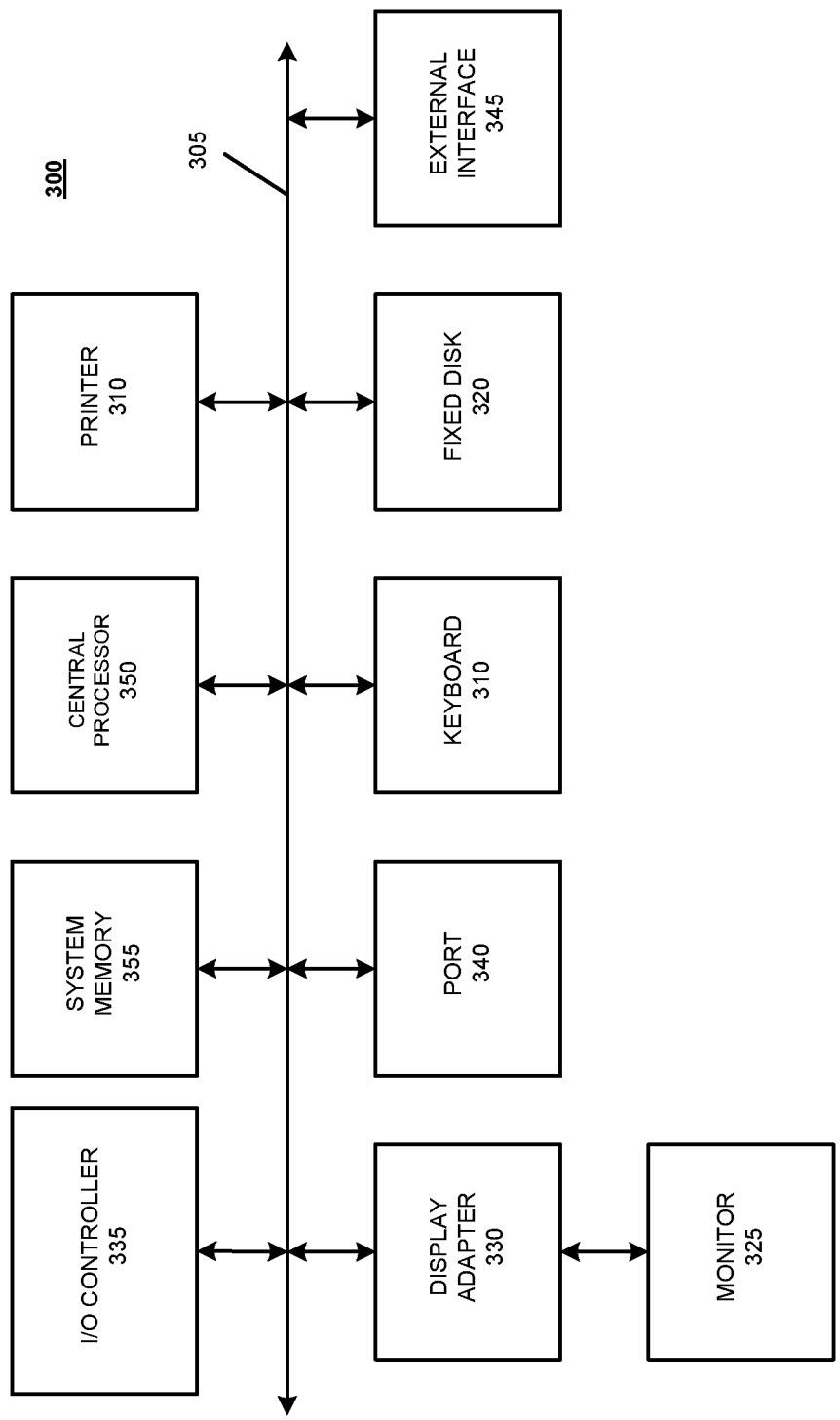
FIG. 3 is a schematic layout of a computing system for use with the methods and systems disclosed herein.

FIG. 3 is a high level block diagram of a computing system 300 that may be used to implement any of the entities or components described above, which may include one or more of the subsystems or components shown in FIG. 3. The subsystems shown in FIG. 3 are interconnected via a system bus 305. Additional subsystems such as a printer 310, keyboard 315, fixed disk 320, monitor 325, which is coupled to display adapter 330, and others are shown. Peripherals and input/output (I/O) devices, which couple to an I/O controller 335, can be connected to the computing apparatus 500 by any number of means known in the art, such as port 340. For example, port 340 or external interface 345 can be used to connect the computing apparatus 300 to a wide area network such as the Internet, a mouse input device, or a scanner. The interconnection via the system bus 305 allows the central processor 350 to communicate with each subsystem and to control the execution of instructions from system memory 355 or the fixed disk 320, as well as the exchange of information between subsystems. The system memory 355 and/or the fixed disk 320 may embody a computer readable medium.

It should be understood that the present invention as described above can be implemented in the form of control logic using computer software in a modular or integrated manner. Based on the disclosure and teachings provided herein, a person of ordinary skill in the art can know and appreciate other ways and/or methods to implement the present invention using hardware and a combination of hardware and software.

Any of the software components, user interfaces, or methods described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

What is claimed is:

1. A cytometry system comprising:
a processor;
a plurality of lasers controlled by the processor to emit laser light, each laser being spatially separated along a flow stream path;
a detector system configured to receive light pulses from the plurality of lasers, the detector system being coupled to the processor;
wherein the processor is configured to operate each of the plurality of lasers to independently emit laser light with respect to one another based only on light pulses received, by a single detector of the detector system, from a first laser of the plurality of lasers and time of flight intervals along the flow stream path.

2. The cytometry system of claim 1, wherein the plurality of lasers comprises at least the first laser and a last laser.

3. The cytometry system of claim 2, wherein the processor is configured to turn the first laser ON only when the last laser is OFF.

4. The cytometry system of claim 3, wherein, after turning the first laser ON, the processor is configured to turn the first laser OFF and the last laser ON according to the time of flight intervals.

5. The cytometry system of claim 4, wherein the processor is configured to turn the first laser ON again only after the last laser is turned OFF according to the time of flight intervals.

6. The cytometry system of claim 5, wherein the plurality of lasers further comprises at least a second laser spatially separated between the first and last laser.

7. A method for operating a cytometry system, the method comprising:
flowing a material along a flow stream having a first interrogation point of a first laser spatially separated from a last interrogation point of a second laser, wherein the first laser is turned ON and the second laser is turned OFF;
receiving, at a single detector of a detector system, a first light pulse derived from the first laser interacting with a material at the first interrogation point;
based only on the first light pulse received at the first detector, turning the second laser ON;
receiving, at the single detector, a second light pulse derived from the second laser interacting with the material; and
based only on the second light pulse received at the first detector, turning the second laser OFF.

8. The method of claim 7, further comprising based only on the second light pulse received at the first detector, turning the first laser back ON.

9. The method of claim 7, wherein the flow stream includes a third interrogation point of at least a third laser downstream from the second interrogation point.

10. The method of claim 9, further comprising based only on the second light pulse received at the first detector, turning the third laser ON.

11. The method of claim 10, further comprising receiving, at the one or more detectors, a third light pulse derived from the third laser interacting with the material.

12. The method of claim 11, further comprising based only on the third light pulse received at the first detector, turning the third laser OFF.

13. The method of claim 12, further comprising based only on the third light pulse received at the first detector, turning the first laser back ON.

* * * * *